United States Patent
Vrba et al.

(10) Patent No.: US 6,544,278 B1
(45) Date of Patent: Apr. 8, 2003

(54) ROLLING MEMBRANE STENT DELIVERY SYSTEM

(75) Inventors: Anthony C. Vrba, Maple Grove, MN (US); Lance A. Monroe, New Hope, MN (US); Scott R. Smith, Chaska, MN (US); David J. Sogard, Edina, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 249 days.

(21) Appl. No.: 09/711,687

(22) Filed: Nov. 10, 2000

Related U.S. Application Data (63) Continuation-in-part of application No. 09/502,682, filed on Feb. 11, 2000, now Pat. No. 6,238,410, which is a continuation of application No. 09/187,947, filed on Nov. 6, 1998, now Pat. No. 6,059,813.

(51) Int. Cl.[7] ............................................. A61M 29/00
(52) U.S. Cl. ...................................... 606/198; 606/192
(58) Field of Search ............................... 606/192, 198, 606/194, 108; 604/96.01

(56) References Cited

U.S. PATENT DOCUMENTS

| | | | |
|---|---|---|---|
| 4,732,152 A | 3/1988 | Wallsten et al. ............ 128/343 |
| 4,793,348 A | * 12/1988 | Palmaz ....................... 606/194 |
| 4,848,343 A | 7/1989 | Wallsten et al. ............ 128/343 |
| 4,875,780 A | 10/1989 | Imbert ........................ 122/313 |
| 5,071,407 A | 12/1991 | Termin et al. ............... 604/104 |
| 5,178,618 A | 1/1993 | Kandarpa .................... 604/104 |
| 5,201,757 A | 4/1993 | Heyn et al. .................. 606/198 |
| 5,221,261 A | 6/1993 | Termin et al. ............... 604/104 |
| 5,344,426 A | * 9/1994 | Lau et al. .................... 606/198 |
| 5,378,239 A | 1/1995 | Termin et al. ............... 604/104 |
| 5,445,646 A | 8/1995 | Euteneuer et al. .......... 606/198 |
| 5,496,277 A | 3/1996 | Termin et al. ............... 604/104 |
| 5,500,181 A | * 3/1996 | Wang et al. ................. 606/194 |
| 5,509,900 A | 4/1996 | Krikman ..................... 604/104 |
| 5,534,007 A | 7/1996 | St. Germain et al. ....... 606/108 |
| 5,571,135 A | 11/1996 | Fraser et al. ................ 606/198 |
| 5,593,418 A | 1/1997 | Mollenauer ................. 606/194 |
| 5,639,274 A | 6/1997 | Fischell et al. .............. 604/96 |
| 5,662,703 A | 9/1997 | Yurek et al. ................. 623/104 |
| 5,690,644 A | 11/1997 | Yurek et al. ................. 606/108 |
| 5,702,364 A | 12/1997 | Euteneuer et al. ........... 604/96 |

(List continued on next page.)

FOREIGN PATENT DOCUMENTS

| | | |
|---|---|---|
| DE | 42 42 291 A1 | 6/1994 |
| EP | 278333 | 4/1992 |
| EP | 0 684 022 | 11/1995 |
| WO | 92/12681 | 8/1992 |
| WO | 93/17747 | 9/1993 |
| WO | 93/19703 A1 | 10/1993 |
| WO | 94/15549 | 7/1994 |
| WO | 95/10317 | 4/1995 |
| WO | 95/23563 | 9/1995 |
| WO | 96/32078 | 10/1996 |
| WO | 97/16133 | 5/1997 |
| WO | 98/07387 | 2/1998 |
| WO | 98/52496 | 11/1998 |
| WO | 00/27309 | 5/2000 |
| WO | 01/78627 | 10/2001 |

OTHER PUBLICATIONS

U.S patent application Ser. No. 09/502,682, Vrba et al., filed Feb. 11, 2000

*Primary Examiner*—Rodney M. Lindsey
(74) *Attorney, Agent, or Firm*—Vidas, Arrett & Steinkraus P.A.

(57) ABSTRACT

A medical device delivery system, having a rolling retractable sheath covering a medical device mounting region on the system is disclosed. The rolling retractable sheath comprises an inner wall and an outer wall and may be formed of one or more materials, optionally porous. Optionally, a lubricant may be applied selectively to the interior and exterior walls of the stent.

17 Claims, 10 Drawing Sheets

U.S. PATENT DOCUMENTS

| | | | |
|---|---|---|---|
| 5,769,821 A | 6/1998 | Abrahamson et al. | 604/104 |
| 5,800,517 A | 9/1998 | Anderson et al. | 623/1 |
| 5,833,657 A * | 11/1998 | Reinhardt et al. | 606/192 |
| 5,935,135 A * | 8/1999 | Bramfitt et al. | 606/192 |
| 6,059,813 A | 5/2000 | Vrba et al. | 606/198 |
| 6,071,263 A | 6/2000 | Kirkman | 604/104 |
| 6,083,257 A | 7/2000 | Taylor et al. | 623/1 |
| 6,123,720 A | 9/2000 | Anderson et al. | 623/1 |
| 6,183,508 B1 * | 2/2001 | Stinson et al. | 604/96.01 |
| 6,280,412 B1 * | 8/2001 | Pederson et al. | 606/108 |
| 6,464,718 B1 * | 10/2002 | Miller et al. | 606/198 |

* cited by examiner

ROLLING MEMBRANE STENT DELIVERY SYSTEM

CROSS-REFERENCE TO RELATED APPLICATIONS

This application is a Continuation-in-part Application of U.S. application Ser. No. 09/502,682, filed Feb. 11, 2000 which issued on May 29, 2001 as U.S Pat. No. 6,238,410, which is itself a Continuation Application of U.S. application Ser. No. 09/187,947, filed Nov. 6, 1998 which issued on May 9, 2000 as U.S. Pat. No. 6,059,813. The entire content of of U.S. Pat. No. 6,238 410 and U.S. Pat. No. 6,059,813 being incorporated in their entirety herein by reference.

STATEMENT REGARDING FEDERALLY SPONSORED RESEARCH

Not Applicable

BACKGROUND OF THE INVENTION

This invention relates to a stent delivery and dilation catheter system, such as the kind used in percutaneous transluininal coronary angioplasty (PTCA) procedures. More particularly, it relates to a stent delivery catheter employing a rolling retractable sheath which may be retracted to release a self-expanding or balloon expandable stent and which may also be employed as a dilatation balloon for expanding a vessel prior to stent delivery.

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. A balloon catheter is advanced over the guide wire to the treatment site. The balloon is then expanded to reopen the artery. The catheter may have a guide wire lumen which is as long as the catheter (such as with an over the wire catheter—OTW) or it may be a rapid exchange catheter wherein the guide wire lumen is substantially shorter than the catheter. Alternatively, a fixed wire balloon catheter could be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to the expand the stent. The self-expanding stents may be made of shape memory materials such as Nitinol or constructed of other metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is retracted to expose the stent. After the sheath is removed, the stent is free to self-expand or be expanded with a balloon.

A number of sheath designs are known in the art including those disclosed in U.S. Pat. No. 4,732,152 to Wallsten ('152), U.S. Pat. No. 4,848,343 to Wallsten ('343), U.S. Pat. No. 4,875,480 to Imbert, U.S. Pat. No. 5,662,703 to Yurek et al. ('703), U.S. Pat. No. 5,690,644 to Yurek ('644) and WO 94/15549, all of which are respectively incorporated herein in their entirety by reference, disclose using a sleeve formed of a doubled-over section of membrane to compress and contain the stent.

Wallsten '152 and Wallsten '343 disclose the use of lubricants on the interior walls of the membrane. Moreover, fluid may be introduced into the chamber that is formed, in part, by the walls of the doubled-over membrane.

The Imbert device contains small holes in the sleeve to allow for the expulsion of gas therefrom upon the introduction of a fluid into the region between the inner and outer walls. The holes are not sized to allow for fluid flow therethrough.

Yurek '703 discloses a stent that is retained distal to the inner tube by a folded over sheath. The outer layer of the sheath, although not the inner layer, is disclosed as being porous. The Yurek '644 patent and WO 94/15549 disclose a catheter in which a stent is mounted on an inner tube and retained by a double walled hose having micro pores in the outer wall of the hose. The micro pores allow for the flow of fluid therethrough. The Yurek catheter is of the rapid-exchange design.

U.S. Pat. No. 5,445,646 to Euteneuer et al., incorporated herein in its entirety by reference, discloses a stent delivery apparatus comprising a single layer sheath retaining sleeve means for retaining the stent in its delivery configuration attached to a slipping sleeve means for releasing the stent to self-expand. The slipping sleeves may be activated hydraulically by delivering a fluid to the area in between the inner and outer layers of the slipping sleeve.

While the use of rolling membranes is known, it is desirable to provide a medical device delivery system with a rolling retractable sheath in which the frictional interactions between the inner and outer walls of the sheath are reduced without requiring hydraulic activation. A rolling membrane eliminates the problem of sliding friction that is common with sliding sheaths as the rolling membrane, literally, rolls off of the stent. This, in turn, results in a lesser likelihood of the stent being damaged as the sheath is removed from over it. It is also desirable to provide a dual function stent delivery system wherein the sheath may function as an expansion balloon as well as a stent retaining sheath. It is also desirable to provide such a system with a partially sealed rolling retractable sheath to prevent any lubricants or inflation fluids interior to the sheath from interacting with any bodily fluids. It is also desirable to provide a system having a rolling retractable sheath whose inner and outer walls exhibits different physical properties such as hoop strength, expansion characteristics and creep resistance. The creep resistance of the outer wall is of particular value in preventing the stent from growing in profile and thereby deforming the catheter sheath.

The present invention addresses these needs in its various embodiments as described below.

SUMMARY OF THE INVENTION

The present invention provides a medical device delivery system which comprises an inner tube having a medical device mounting region at the distal region for concentrically mounting a medical device thereon and a rolling retractable sheath which may operate as a dilatation balloon and which retains a medical device on the inner tube and a retraction device.

The rolling retractable sheath, which includes a rolling double walled member, may be formed of a single member folded over on itself or of two different members joined together and folded over on itself. It is disposed concentrically about the inner tube. The inner wall of the double walled member is attached to the inner tube proximal to the medical device mounting region and the outer wall of the double walled member is attached to a retraction device. The inner wall preferably has a greater tendency to rollingly move upon the application of a rolling force than the outer wall.

An open ended chamber is formed by the inner and outer walls of the sheath. The open end of the chamber narrows at a point where it is in fluid communication with a proximally extending inflation lumen. The chamber may be filled with a fluid in order to cause at least the outer wall of the sheath to expand outward from the catheter. The various walls of the catheter may be constructed to allow the outer wall to have predetermined inflation properties which may differ from those of the inner wall.

The inner tube has a medical device mounting region at the distal region for concentrically mounting a medical device thereon. The sheath is retractable from a delivery position to a release position. In the delivery position, the sheath covers at least a portion of the medical device mounting region while in the release position, the sheath no longer covers the medical device mounting region.

The retraction device, which is operably connected to the rolling retractable sheath for retraction of the retractable sheath, moves the outer wall in a proximal direction relative to the inner wall so that the sheath no longer covers the medical device mounting region. When the sheath is used as dilatation balloon, during inflation of the sheath the retraction device may be used to position the sheath and to assist in preventing the sheath from moving off of the stent prior to delivery of the stent.

In another embodiment, the invention is directed to a medical device such as those described above in which the inner wall of the rolling retractable sheath is formed of at least a first material and the outer wall is formed of at least a second material different from the first material. The inner and outer walls may be adhesively bonded together, mechanically joined together or otherwise joined to each other.

In another embodiment, the inner and outer walls, respectively, may be constructed of a first material which rolls on retraction of the sheath and a second material which does not roll on retraction. In another embodiment the second material has a higher hoop strength than the first material. In yet another embodiment the outer wall material has a higher tensile strength than the inner wall material of the sheath. In yet another embodiment the outer wall exhibits a higher degree of longitudinal stiffness than the inner wall. In yet another embodiment the outer wall is more compliant than the inner wall. In yet another embodiment the outer wall exhibits a higher flexural modulus than the inner wall.

In the above embodiments where the inner and outer walls are made of different materials, the thickness of the inner and outer walls may also differ, further contributing to the desired properties of the walls.

In yet another embodiment of the invention, the inner and outer walls are made of the same material, the inner wall being thinner than the outer wall. The inner wall is thin enough to allow the inner wall to roll while the outer wall is sufficiently thick to resist rolling and prevent unwanted movement of the stent. Desirably, the thickness of the outer wall will be at least 1.5 times the thickness of the inner wall, more desirably, the outer wall will be at least 4 times the thickness of the inner wall.

In all of the above embodiments, a lubricant may, optionally, applied to at least a portion of the inner wall and/or outer wall.

Further, in all of the above embodiments, a pull-collar mounted at the distal end of the catheter in conjunction with a pull wire may be employed as part of the retraction device.

The invention is further directed to a stent delivery device comprising any of the above-described medical device delivery systems with a stent mounted on the medical device mounting region of the inner tube. Other device that may be delivered by the above described systems include grafts and vena cava filters.

The invention is also directed to a method of delivering a medical device to a desired bodily location. The method comprises the steps of providing medical device delivery system and a medical device, mounting the medical device on the medical device mounting region of one of the described medical device delivery systems, percutaneously inserting the medical device delivery system in a bodily lumen containing a bodily fluid, the bodily fluid optionally passing through the sheath so as to prime the medical device delivery system, traversing the bodily lumen until the desired bodily location is reached, optionally inflating the sheath to pre-dilate the body lumen, retracting the rolling retractable sheath proximally so as to expose the medical device and withdrawing the medical device delivery system from the bodily lumen. In a preferred embodiment, the medical device is a stent, optionally self-expanding, although other devices including grafts and vena cava filters may be similarly delivered.

Finally, the invention is directed to a medical device delivery system comprising an inner tube having a medical device mounting region at the distal region for concentrically mounting a medical device thereon, a rolling retractable sheath and a retraction device for retracting the rolling sheath. The rolling retractable sheath serves to retain a medical device around for about the inner tube. The rolling retractable sheath is formed of a double walled member forming an open chamber between the walls which is inflatable by being in fluid communication with a proximally extending inflation lumen. The sheath is disposed concentrically about the inner tube. At the proximal end, the rolling sheath is secured, directly or indirectly via a bumper or other securement device, to the inner tube proximal of the medical device mounting region. At the distal end, the rolling sheath is attached to a retraction device.

For the purposes of this disclosure, it should be noted that the term "medical device mounting region" is intended to apply to a region of an inner tube on which a medical device resides as well as a region of an inner tube over which a medical device resides. An example of the former is a region of an inner tube to which a stent is crimped. An example of the latter is a region over which a self expanding stent resides. Moreover, where reference is made to mounting a medical device on an inner tube, it is intended to include both mounting the device on and mounting the device over the inner tube.

BRIEF DESCRIPTION OF THE FIGURES

FIG. 1b shows a partial exploded view of circled region 1b in FIG. 1a.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1A:
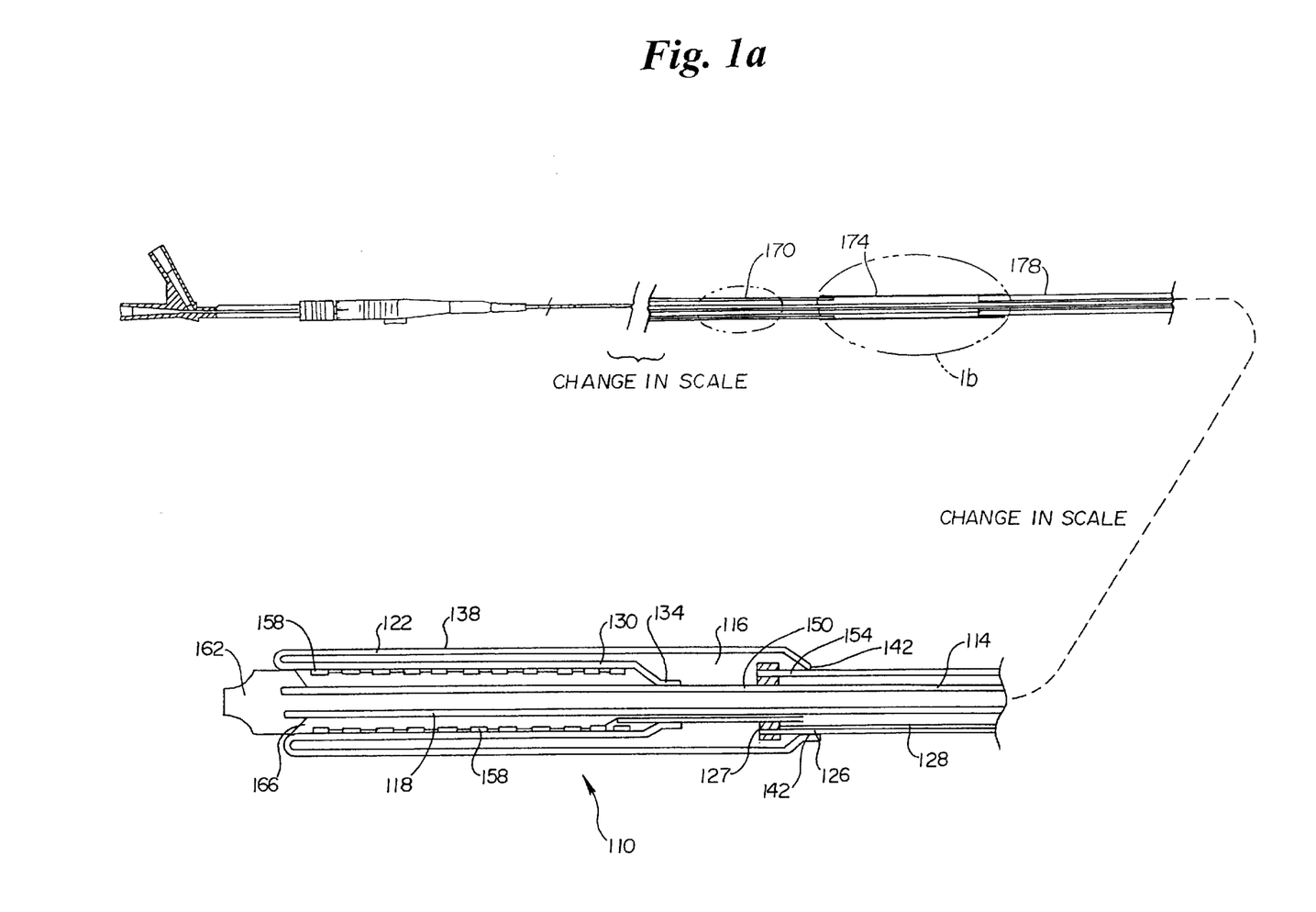
FIG. 1a shows a schematic longitudinal cross-sectional view of inventive medical device delivery system.

Referring to the figures, FIG. 1a shows an inventive medical device delivery system in general at 110. At the distal end of inner tube 114 is a medical device mounting region 118. Inner tube 114 is desirably made of flexible, but incompressible construction such as a polymer encapsulated braid or coil. The flexibility of the braid/coil construction allows the medical device delivery system to navigate through body lumens and the incompressibility of the braid/coil aids in maintaining the integrity for the catheter and aids in deployment accuracy when the retractable rolling sheath is being retracted during stent release. The braid/coil may be comprised of stainless steel encased in a polymer such as Polyimide with an inner layer of Teflon. The inner tube need not, however, be made of incompressible materials. Flexible and compressible materials such as polyethylene may also be used.

Covering medical device mounting region 118 is a rolling retractable sheath 122 for retaining a medical device on the inner tube. The medical device delivery system further comprises a retraction means for retracting the rolling retractable sheath.

Figure 2:
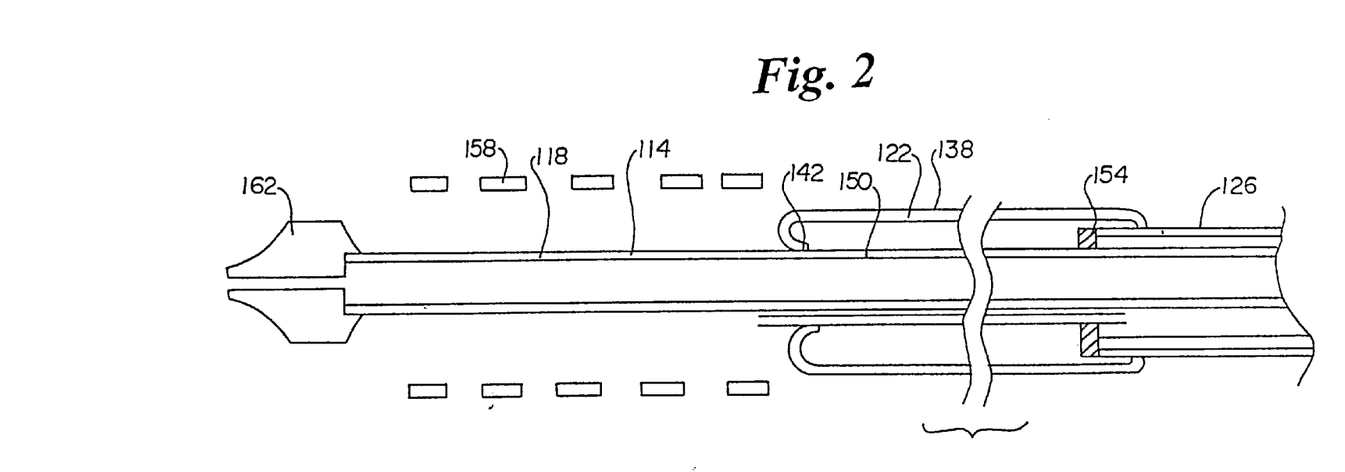
FIG. 2 shows the distal end of the inventive medical device delivery system of FIG. 1 with the rolling retractable sheath in a retracted position.

Rolling retractable sheath 122, disposed concentrically about inner tube 114, is formed of a single material folded over on itself. As such, at least a portion of the sheath is double-walled. Inner wall 130 of sheath 122 is attached to inner tube 114 at a region 134 proximal to medical device mounting region 118. Outer wall 138 of sheath 122 is attached to retraction device 126 at region 142 of the retraction device. A sealed chamber 146 is formed by inner wall 130 and outer wall 138 of the sheath, at least a portion 150 of the inner tube and the portion 154 of the retraction device which is distal to the region of attachment 142 of the outer wall to the retraction device. The sheath is retractable from a delivery position, as shown in FIG. 1a, to a release position as shown in FIG. 2. In the delivery position, the sheath covers at least a portion of the medical device mounting region while in the release position, the sheath no longer covers the medical a device mounting region.

A retraction device 126 is attached to rolling retractable sheath 122. Retraction device 126 comprises a pull collar 127 operably attached to a pull-wire 128 which extends to the proximal end of the medical device delivery system. Pull collar 127 is a ring-shaped member of stainless steel or preferably of a radio-opaque material such as gold affixed to distal outer tube 178 by an appropriate adhesive such as a urethane. The distal outer tube is, in turn, connected to the rolling sheath. The pull wire may be made of suitable material including stainless steel.

Figure 1B:
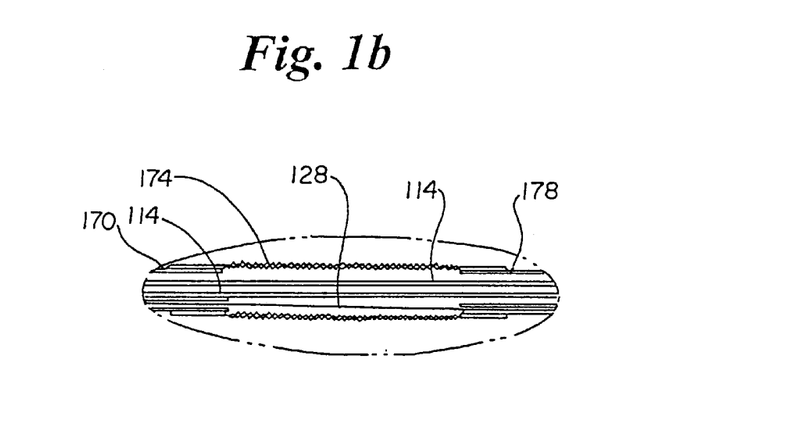

The inventive medical device delivery system, optionally, further comprises a collapsible midshaft sheath, as shown in FIG. 1a and in more detail in FIG. 1b. The distal end of proximal outer tube 170 is attached, desirably adhesively bonded, to an accordion-like collapsible midshaft sheath 174. The distal end of collapsible midshaft sheath 174 is, in turn, attached, desirably adhesively bonded, to distal outer tube 178. Pull collar 127 is attached to the distal end of distal outer tube 178. In operation, the retraction device/moves the outer wall in a proximal direction relative to the inner wall so that the sheath no longer covers the medical device mounting region. In so doing, collapsible midshaft sheath 174 decreases in length. Additional information about the collapsible midshaft sheath made be found in U.S. Pat. No. 5,534,007 to St. Germain and Olson, incorporated herein in its entirety by reference.

Rolling retractable sheath 122 is retractable from a delivery position as shown in FIG. 1, to a release position as shown in FIG. 2.

As seen in FIG. 1a, the medical device delivery system further comprises an optional tip 162 mounted at the distal end of inner tube 114 abutting retractable sheath 122. Tip 162 may be affixed to the inner tube by an adhesive such as H. B. Fuller 3507, a urethane adhesive, or the like.

Also shown in the embodiment of FIG. 1a is a self-expanding stent 158 mounted on medical device mounting region 118 of the system. Stent 158 is contained in medical device containment area 166.

Because sealed chamber 146 is not in fluid communication with any part of the delivery system proximal of the sheath, the sealed chamber may be coated or filled with a lubricating substance to reduce the friction between the inner and outer walls of the sheath without any direct interaction between the lubricating substance and a bodily fluid.

Figure 3:
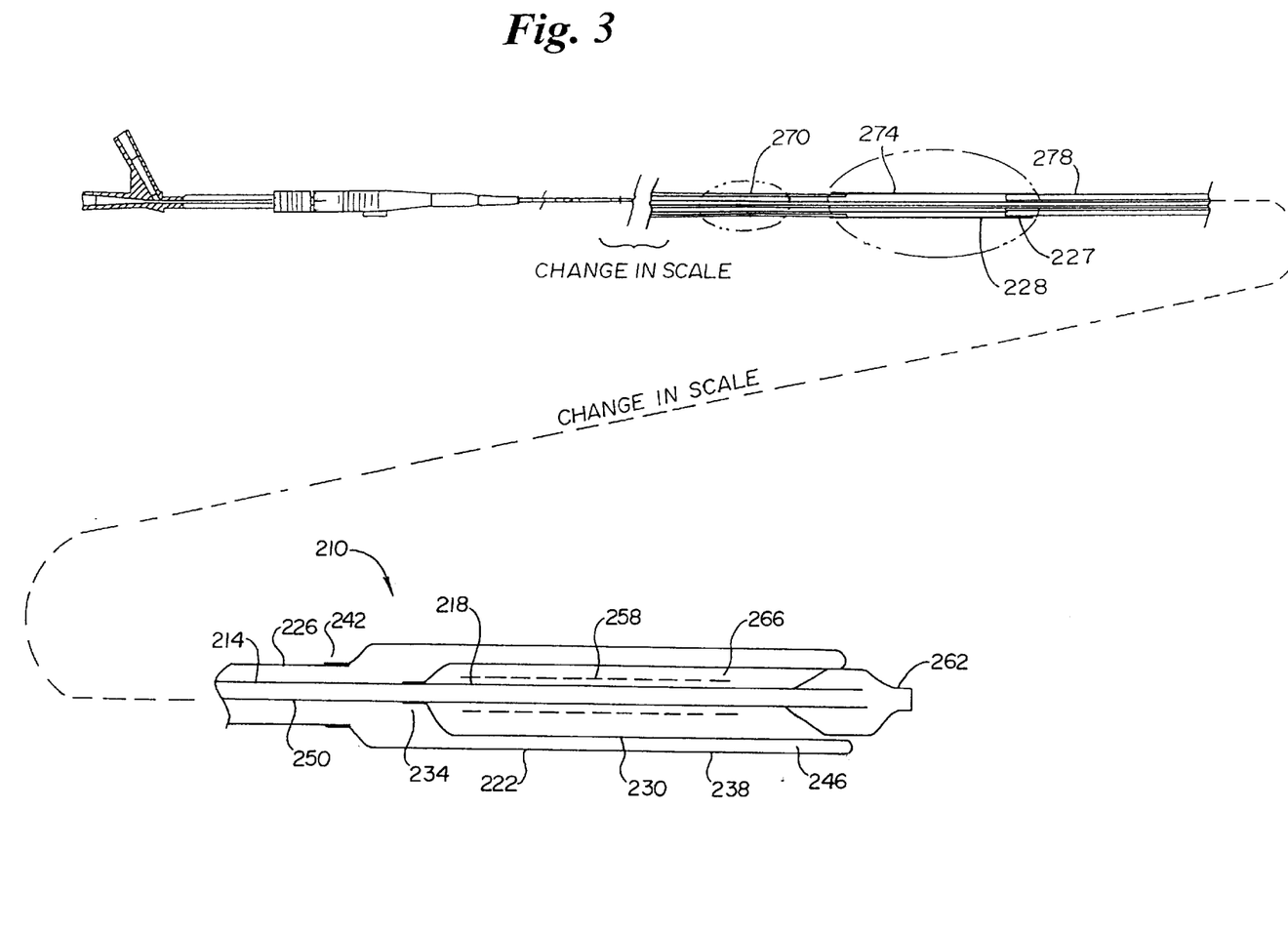
FIG. 3 shows a schematic longitudinal cross-sectional view of the distal end of an inventive medical device delivery system.

In another embodiment of the invention, as shown in FIG. 3, the medical device delivery system shown generally at 210 comprises an inner tube 214 with a medical device mounting region 218 at the distal end of inner tube. Covering medical device mounting region 218 is a rolling retractable sheath 222 for retaining a medical device on the inner tube. Attached to rolling retractable sheath 222 is a retraction device 226 for retracting the sheath.

As in the previous embodiment, rolling retractable sheath 222, is formed of a single material folded over on itself. Inner wall 230 of sheath 222 is attached to inner tube 214 at a region 234 proximal to medical device mounting region 218. Outer wall 238 of sheath 222 is attached to retraction device 226 at region 242 of the retraction device. As before, retraction device 226 includes proximal outer tube 270 attached to retractable sheath 274 which in turn is attached to distal outer tube 278. Pull collar 227 is attached to the distal end of the distal outer tube 278 and pull wire 228 extends proximally from pull collar 227.

Also shown in the embodiment of FIG. 3 is an optional self-expanding stent 258 mounted on medical device mounting region 218 of the system. Stent 258 is contained in medical device containment area 266.

Although sheath 274 in the unretracted position, as shown in FIG. 3, is shown as being double walled over the entire length of stent 258, the double walled region of the sheath need not extend over the entire length of the stent but may extend over only a fraction of the stent. Using a sheath whose doubled over region in the unretracted position is of reduced length may prove advantageous in that the overall length of the sheath in the retracted position is also reduced thereby resulting in a delivery system with a smaller profile over a greater length. It is desirable for the double over region to extend over at least one-half of the stent and more desirable to extend over at least one quarter or one eighth of the stent.

Optionally, the chamber 246 formed by inner wall 230 and outer wall 238 of the sheath and at least a portion of the inner tube 250 and a portion of the retraction device 226 may be sealed.

As seen in FIG. 3, the medical device delivery system further comprises an optional tip 262 mounted at the distal end of inner tube 214 abutting retractable sheath 222.

In the embodiment shown in FIG. 3, the rolling sheath 222 is made, at least in part, of a porous material capable of allowing fluid therethrough. Suitable porous materials include expanded polytetrafluoroethylene (ePTFE) and polyester. Desirably, the materials will have a pore size ranging from 0.01 mm to 5.0 mm.

The porosity of the inner and outer walls allows medical device containment area 266 to be flushed free of air by fluid traveling through the inner and outer walls and into the medical device containment area.

Figure 4:
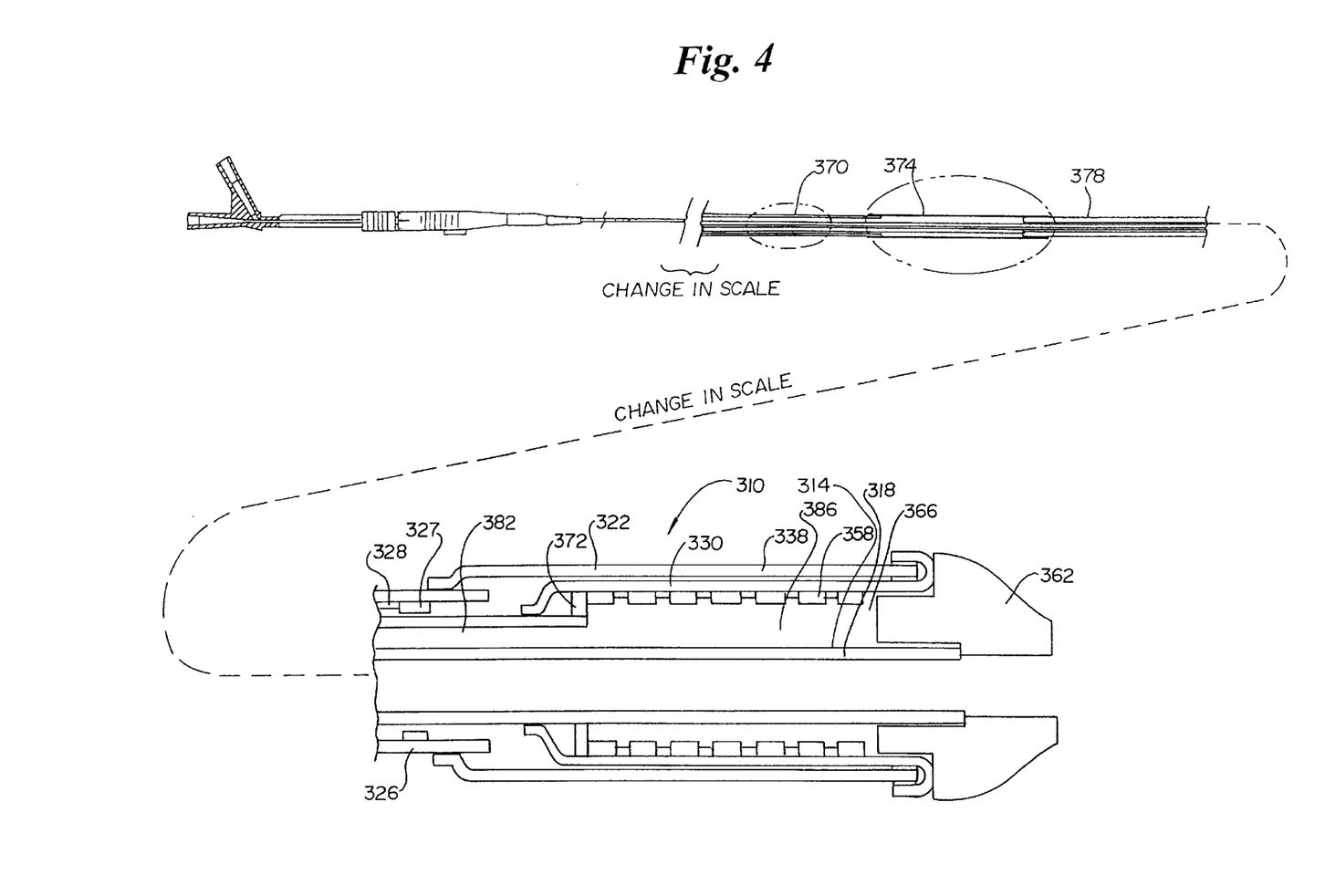
FIG. 4 shows a schematic longitudinal cross-sectional view of the distal end of an inventive medical device delivery system.

In yet another embodiment, as shown in FIG. 4, the inventive medical device delivery system, shown generally at 310, is constructed similarly to the embodiment of FIG. 2, differing in that rolling sheath 322 has an inner wall 330 and an outer wall 338, the inner wall formed of at least a first material, and the outer wall formed of at least a second material different from the first material. The delivery system of FIG. 4 further differs from the delivery system of FIG. 3 in that inner tube 314 is comprised of part of a dual lumen tube. The other lumen 382 of the dual lumen tube provides for a flush lumen in fluid communication with stent chamber 386.

As before, retraction device 326 includes proximal outer tube 370 attached to retractable sheath 374 which in turn is attached to distal outer tube 378. Pull collar 327 is attached to the distal end of the distal outer tube 378 and pull wire 328 extends proximally from pull collar 327.

As seen in FIG. 4, the medical device delivery system further comprises an optional tip 362 mounted at the distal end of inner tube 314 abutting retractable sheath 322.

Also shown in the embodiment of FIG. 4 is a self-expanding stent 358 mounted on medical device mounting region 318 of the system. Stent 358 is contained in medical device containment area 366. Optional bumper 372 is also shown. Bumper 372 may be of polyethylene and is affixed to the inner tube by an adhesive such as H. B. Fuller 3507.

Additionally, the medical device delivery system may comprise marker bands (not shown) included to aid in positioning and maybe affixed to the inner tube by adhesive such as Loctite 4011.

Inner wall 330 and outer wall 338 may be adhesively bonded together, heat welded, sutured or otherwise mechanically joined together. Suitable adhesives include urethane and epoxy.

While the invention contemplates a wide variety of choices for first and second materials, the materials must be chosen such that the material of the inner wall will have a greater tendency to rollingly move upon the application of a rolling force than the outer wall. For the purposes of this application, the relative tendency of materials to rollingly move may be tested by taking a strip of a given material, immobilizing one end of the strip, folding a small portion of the opposite end of the material over on itself and measuring the force in the longitudinal direction necessary to initiate rolling motion of the folded over end of the material.

Desirably, a first material that rolls on retraction of the sheath will be selected along with a second material that does not roll on retraction. Desirably, the second material will have a higher hoop strength than the first material. Also, desirably, the outer wall of the sheath in the unretracted position has a higher tensile strength than the inner wall of the sheath. In a preferred embodiment, the outer material is made of high density polyethylene (HDPE) and the inner material is made of poly(block-amide-block-ether) ester materials such as PEBAX™ brand polymers manufactured by Atochem North America, Inc. (Philadelphia Pa.).

The materials may also be chosen so that the outer layer is resistant to creep in the radial direction and/or resistant to compression or expansion in the longitudinal direction while the inner layer is flexible, both radially and longitudinally. The extra strength of the outer layer prevents the sheath from creeping under the force of a self-expanding stent contained by the sheath and helps to ensure that the stent will not deploy until the system is actuated. At the same time, the flexibility of the inner layer allows the sheath to be rolled in on itself.

The materials may also be chosen such that the outer layer is made of a material of higher tensile strength, flexural modulus and/or higher hoop strength than the inner layer. The materials may also be chosen such that the outer layer has a higher degree of longitudinal stiffness than the inner layer.

In another embodiment of the invention, the rolling retractable sheath is characterized by the presence of an outer wall of a first thickness and an inner wall of a second thickness. The first thickness may be greater or less than the second thickness. Where the outer wall is thinner than the inner wall, the material of the outer wall must have a flexural modulus and/or tensile strength and/or hoop strength and/or longitudinal stiffness in excess of that of the inner material so that the relative thicknesses of the layers is offset by the relative material properties of the walls.

The invention also contemplates a medical device delivery system having a rolling retractable sheath where the inner wall of the retractable sheath is flexible enough to roll while the outer wall of the retractable sheath is stiff enough to prevent unwanted movement of the stent and the outer and inner walls are made of the same material. The property differentiation results from the inner wall being thinner than the outer wall. This may be accomplished, for example, by providing a tapered tube folded over on itself.

The invention also contemplates the use of porous materials for the first and/or second materials. Where both materials are porous, the medical device delivery system will be self-priming. Suitable porous materials for use in this embodiment include ePTFE, polyester, and silicone.

In a more general way, the invention contemplates the use of thermoplastic elastomers such as polyurethane, polyethylene, polyester, polyvinyl chloride, nylon and their block copolymers as well as PEBAX™ polymers for the double walled sheath. Other suitable materials include fluoropolymers, non-compliant polyethylene terephthalate (PET), polyimide and polyolefin copolymers such as SUR-LYN™.

Typically, the materials for use in the double walled sheaths of the invention will exhibit high strength even for wall thicknesses as small as $\frac{1}{1000}$'s of an inch. Suitable materials include uniaxially oriented films such as are formed by blow molding.

In order to reduce friction between the outer and inner walls, a suitable lubricant, as is known in the art, may be selectively applied to at least a portion of the inner and/or outer walls. The invention also contemplates completely covering the inner and outer walls with a lubricant. Suitable lubricants include silicones, polyvinyl pyrrolidone, and PPO (polypropylene oxide). Additionally, BioSlide™ coating produced by SciMed made be used as well. BioSlide™ is a hydrophilic, lubricious coating comprising polyethylene oxide and neopentyl glycol diacrylate polymerized in a solution of water and isopropyl alcohol in the presence of a photoinitiator such as azobisisobutronitrile. Other hydrogels such as PEG (polyethylene glycol), PEO/PPO/PEO—polyethylene oxide/polypropylene oxide/polyethylene oxide triblock polymer manufactured by BASF or PPO/PEO/PPO may also be used. Fluids, desirably bio-compatible, may also be used as lubricants in the practice of the invention. The presence of a fluid between the inner and outer walls of the sheath prevents the inner and outer walls from contacting one another thereby reducing the friction between the walls.

Figure 5A:
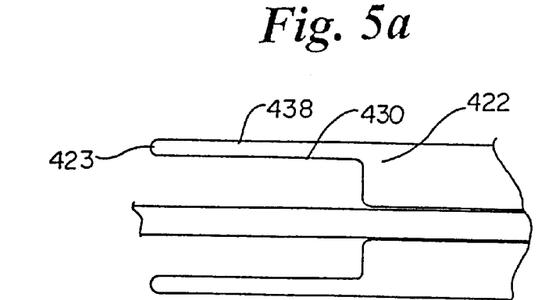
FIGS. 5a and 5b shows schematics of rolling retractable sheaths for use in the present invention.
Figure 5B:
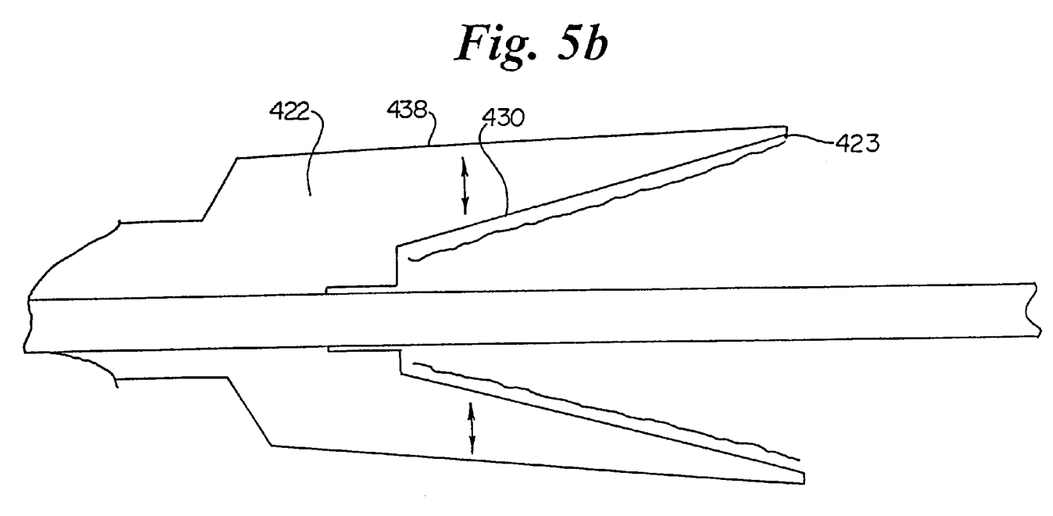

Friction between the inner and outer walls may also be reduced by altering the design of the rolling sheath. The rolling sheath shown in the above figures is reproduced in FIG. 5a. Inner wall 430 and outer wall 438 are substantially parallel to one another. Other, lower friction geometries are also contemplated such as that shown at 422 in FIG. 5b. Inner wall 430 is disposed at an oblique angle relative to outer wall 438 such that the distance between the inner wall and the outer wall increases with the distance from the fold 423 in the rolling sheath. The increased separation between the walls reduces the contact between the walls and hence the frictional interactions between the walls.

Although the use of a flush lumen has only been shown in the embodiment of FIG. 4, it is understood that a flush lumen may suitably be used in any of the other embodiments disclosed herein.

Additional details of the design of embodiments of the inventive medical device delivery system which employ collapsible midshaft sheaths, in particular the portion of the device proximal to the rolling retractable sheath, may be found in the various embodiments disclosed in U.S. Pat. No. 5,534,007 to St. Germain and Olson, incorporated herein in its entirety by reference.

In addition to the use of a collapsible midshaft sheath retraction device for retracting the outer sheath, the invention also contemplates the use of other suitable retraction means as are known in the art including slidably sealed retractable sheaths and midshaft seals as described in co-pending commonly assigned U.S. patent application Ser. No. 08/722,834 filed Sep. 27, 1996 now U.S. Pat. No. 5,772,669, and a continuation-in-part application Ser. No. 09/071,484 filed May 1, 1998 now U.S. Pat. No. 5,957,930. The entire contents of both applications are hereby incorporated in their entirety by reference. Other contemplated retraction means include sheaths activated directly by pull-collars as described in U.S. patent application Ser. No. 09/071,484 filed May 27, 1998, and screw-like retraction devices as described in U.S. Pat. No. 5,201,757 to Heyn et al. all of which are incorporated herein in their entirety by reference.

Alternatively, the rolling retractable sheath may be a full length sheath which extends to the proximal end of the medical device delivery system.

Figure 6:
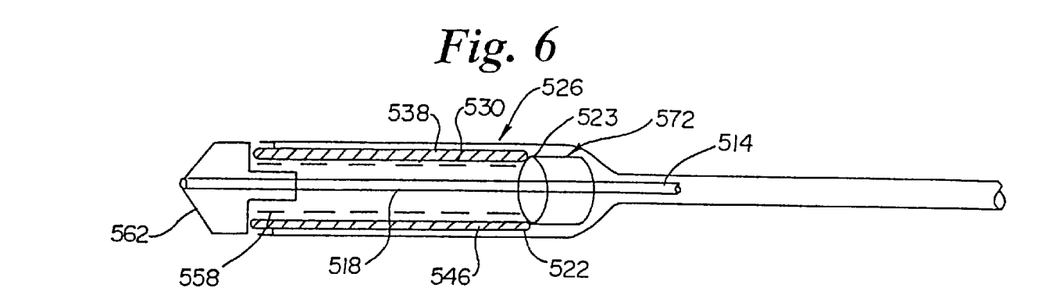
FIG. 6 shows a schematic longitudinal cross-sectional view of the distal end of an inventive medical device delivery system.

In yet another embodiment the invention, as shown generally in FIG. 6, the medical device delivery system comprises a rolling retractable sheath 522 closed on itself. The delivery system comprises an inner tube 514 having a medical device mounting region 518 at the distal region for concentrically mounting a medical device thereon. The proximal end of rolling retractable sheath 522 is secured to the inner tube via optional bumper 572 at a location 523 proximal to medical device mounting region 518. If optional bumper 572 is not present, rolling retractable sheath 522 may be secured directly to the inner tube. Rolling retractable sheath 522 contains stent 558 which is mounted over or around distal end 518 of inner tube 514. Depending on the type of stent used, the stent may alternatively be mounted directly on the inner tube. The distal end of rolling retractable sheath 522 is attached to a retraction device 526. Adhesives such as polyurethane, epoxy, cyanoacrylates and acrylics or other suitable means of attachment including heat welding, suturing or other forms of mechanically joining may be used to affix the rolling sheath to the retraction device. As shown in FIG. 6, retraction device 526 is an outer sheath which covers the rolling sheath and extends in a proximal direction. Rolling retractable sheath 522 may be retracted by pulling outer sheath 526 in a proximal direction.

Rolling retractable sheath 522 may optionally be provided with longitudinally oriented ribs to provide resistance to buckling. Similarly, a tapered sheath design similar to that shown in FIG. 5b and closed on itself at both ends may also be used in order to prevent buckling of the sheath upon retraction of the sheath.

Outer sheath 526 may be a full length sheath which extends all the way to the proximal end of the medical device delivery system or alternatively may extend proximally for only a portion of the delivery system. In the latter case, outer sheath 526 may be used in conjunction with a collapsible midshaft sheath as disclosed above.

The outer sheath may be made of a homogeneous polymer or a composite. Suitable materials include polyolefin copolymers, Pebax, polyurethane, nylon, polyethylene, polyesters and other thermoplastic elastomers. It is desirable for the outer sheath to be flexible, but radially non-compliant. Optionally, the outer sheath may be formed of a polymer encapsulated braid or coil. The braid/coil may be formed of stainless steel encased in a polymer such as Polyimide with an inner layer of Teflon™. Where the outer sheath is made of a polymeric tube, slits may be made in the tube to increase the flexibility of the tube without sacrificing radial strength. The outer sheath may be made from a material which is chosen so as to provide support for the rolling sheath as it is retracted, to prevent distention of the rolling sheath.

Another suitable retraction device is a collar and pull wire. A pull collar, as disclosed above, may be affixed to the distal end of the rolling retractable sheath. A pull wire extending proximally from the pull collar may then be used to retract the rolling sheath. The pull wire may enter the inner tube at a point proximal to the stent and preferably at a point which is at a distance of at least one rolling retractable sheath proximal to the stent so as not interfere with the operation of the rolling sheath.

As discussed above, in conjunction with several of the other embodiments, the rolling sheath may be formed of one material or may be formed of several materials joined together. Because, however, both the inner and outer walls of the rolling sheath roll in this embodiment, it is desirable that both the outer and inner walls be made of the same materials.

As in the other embodiments of the invention, lubricants may be used in the interior of the rolling retractable sheath in the embodiment of FIG. 6 to reduce the frictional interactions between the walls of the sheath and to facilitate rolling. Any of the above lubricants may be employed.

A further advantage of the medical device delivery system shown in FIG. 6 is the reduced length of the rolling sheath upon retraction as compared with rolling sheaths that are not closed on themselves as in the previous embodiments. Whereas the length of a rolling sheath closed on itself is unchanged upon retraction of the sheath, standard rolling sheaths may double in length upon retraction as the sheath is fully extended and ceases to form a double layer. The reduced length of the fully retracted rolling sheath which is closed on itself as compared with a standard rolling sheath allows for a medical device delivery system of lower profile over a greater portion of the distal end of the system.

Figure 7A:
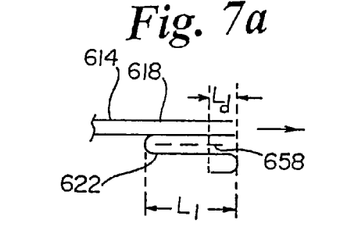
FIGS. 7a and 7b are schematic longitudinal cross-sectional views of a double walled sheath before and after retraction.
Figure 7B:
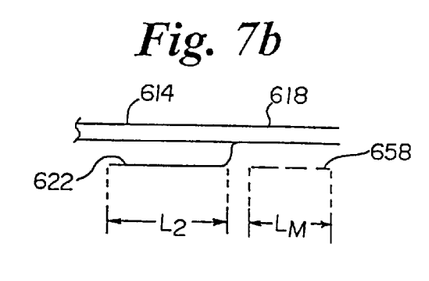
Figure 7C:
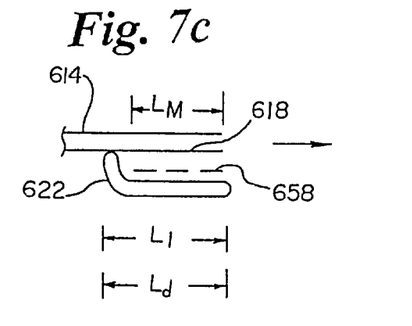
FIGS. 7c and 7d are schematic longitudinal cross-sectional views of a sealed double walled sheath before and after retraction.
Figure 7D:
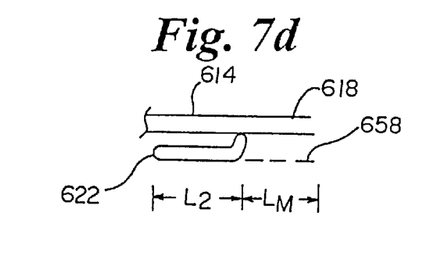

As shown in FIGS. 7a–d, the invention is directed to medical device delivery systems comprising an inner tube 614 with a medical device mounting region 618 at the distal region for concentrically mounting a medical device 658 thereon, a rolling retractable sheath 622 for retaining medical device 658 on medical device mounting region 618 and a retraction device (not shown) for retracting the rolling sheath. As further shown in FIGS. 7a–d, medical device mounting region 618 is characterized by a medical device mounting length, $L_m$. Rolling retractable sheath 622 is disposed about inner tube 614 with the proximal end of rolling sheath 622 secured to inner tube 614 proximal of the medical device mounting region 618. Rolling sheath 622 in an unretracted state, as shown in FIGS. 7a and 7c, is characterized by a first length, $L_1$, as defined by the distance between the proximal-most point on the unretracted sheath and the distal-most point on the unretracted sheath. Rolling sheath 622 in the unretracted state is further characterized by a double wall length $L_d$ as measured by the length over which the sheath forms a double wall. Rolling sheath 622 upon retraction, as shown in FIGS. 7b and 7d, is characterized by a second length, $L_2$, as defined by the distance between the proximal-most point on the retracted sheath and the distal-most point on the retracted sheath. Finally, rolling sheath 622 is operably connected to a retraction device (not shown) for retraction of the rolling sheath.

The delivery system is further characterized in that the difference between the second length $L_2$ and the first length $L_1$ is less than the medical device mounting length $L_m$. Desirably the difference between the second length $L_2$ and the first length $L_1$ will be less than half of the medical device mounting length. More desirably, the difference between the second length $L_2$ and the first length $L_1$ will be substantially equal to zero as in FIGS. 7c and 7d where the rolling sheath is closed on itself or where the sheath has a very short double walled region $L_d$ as in FIGS. 7a and 7b. It is also desirable for the second length $L_2$ to be less than twice the first length $L_1$ and/or less than twice the medical device mounting length $L_m$.

Figure 8:
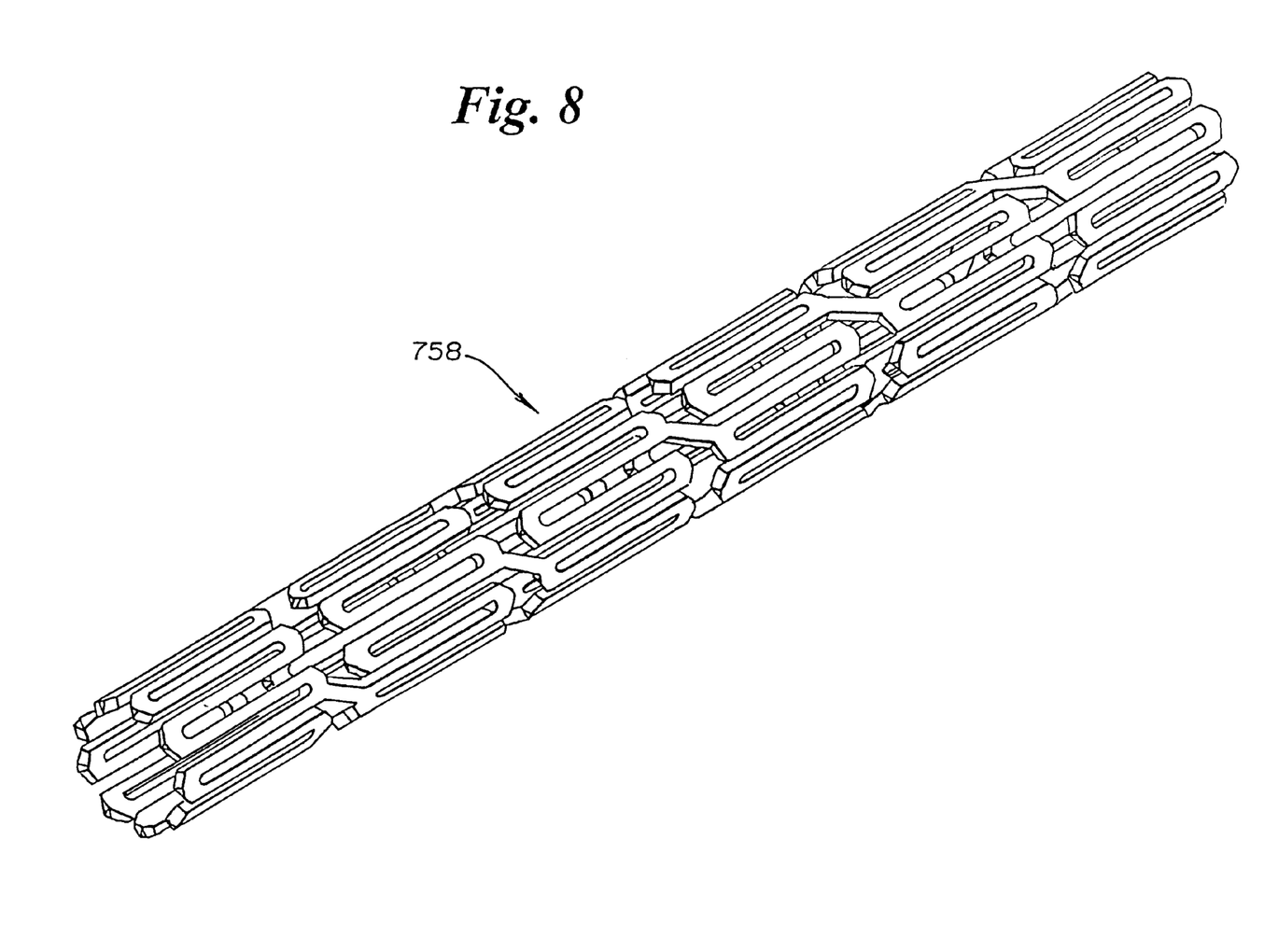
FIG. 8 shows a suitable stent for use with the inventive medical device delivery system.
Figure 9:
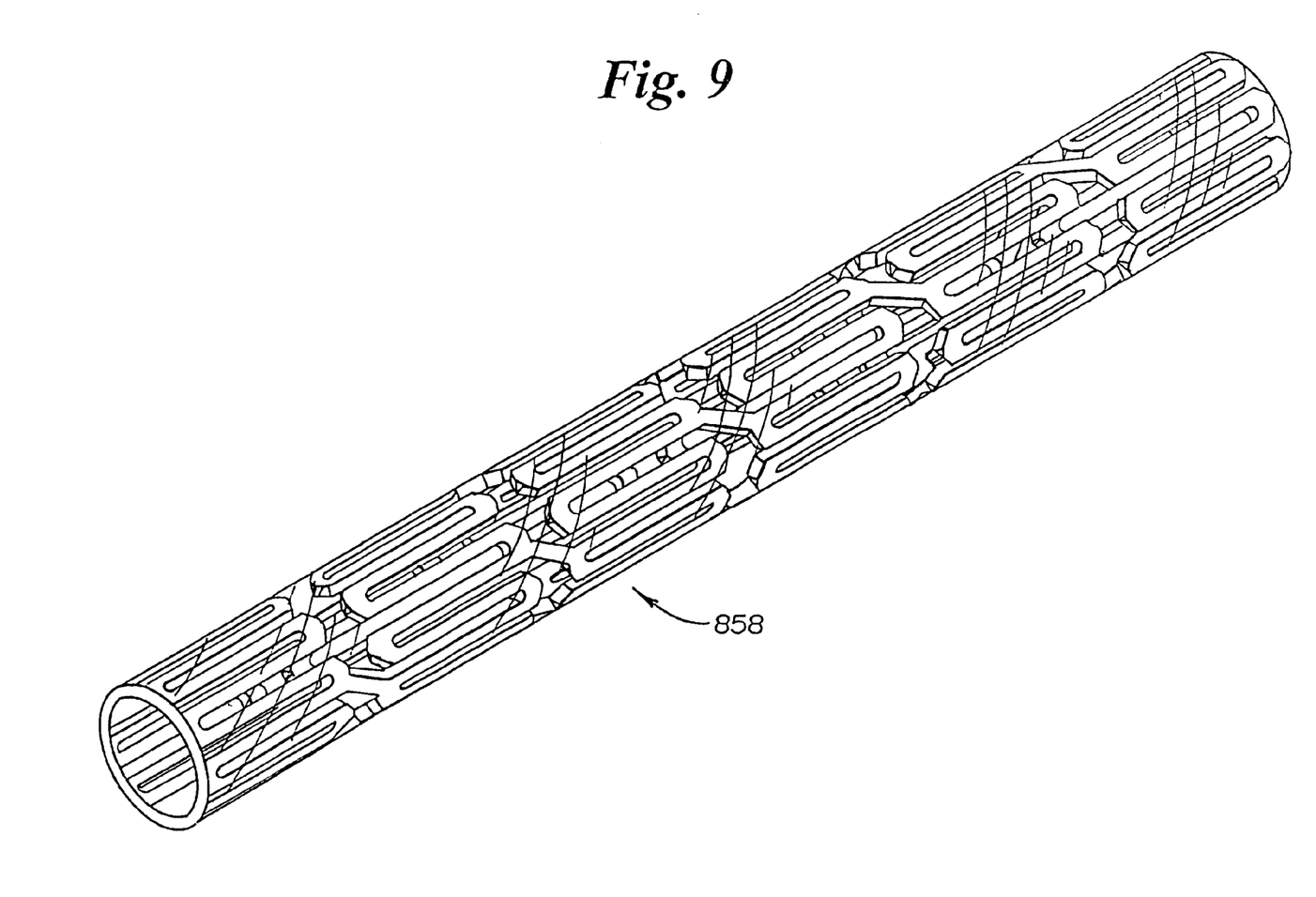
FIG. 9 shows a suitable graft for use with the inventive medical device delivery system.
Figure 10:
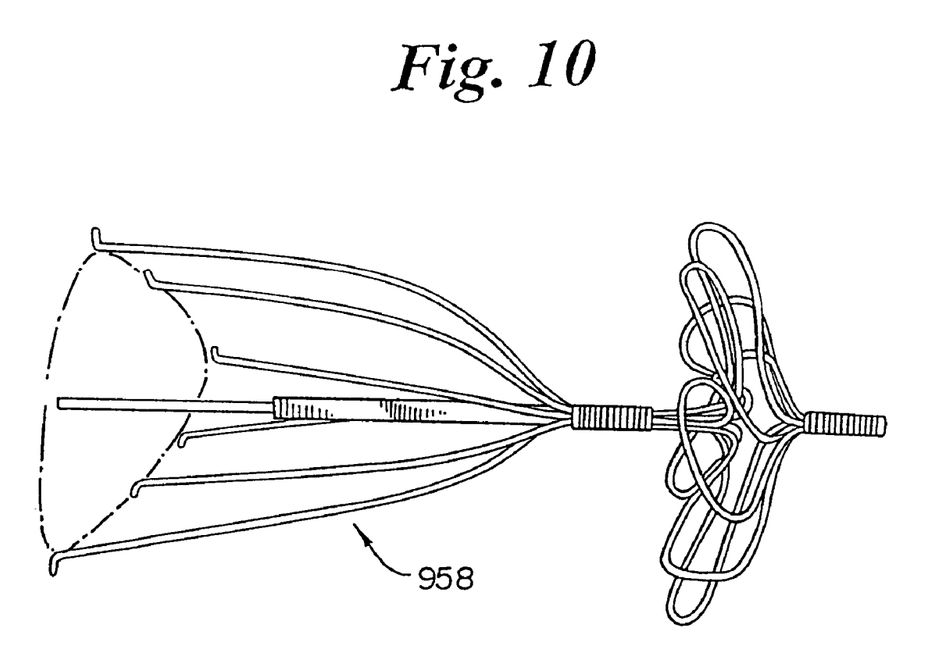
FIG. 10 shows a suitable vena cava filter for use with the inventive medical device delivery system.

Although in a preferred embodiment, the above-disclosed inventive medical devices are used for delivery of self-expanding stents such as that shown in FIG. 8 at 758, other stents may also be used in conjunction with this invention including mechanically expandable stents such as balloon expandable stents. A balloon is provided in the medical device mounting region of the delivery device and a stent mounted thereon. Suitable inflation means as are known in the art, such as an inflation lumen, are provided. Other suitable medical device for use with the present invention include grafts or stents/grafts, including that shown in FIG. 9 at 858 and vena cava filters, including that shown in FIG. 10 at 958.

While the medical devices have been described above as being concentrically mounted about the medical device mounting region of the inner tube, the invention is not intended to be so limited. The invention is directly more generally at a medical device delivery system with a medical device mounted about the medical device receiving region, whether or not the medical device is concentric with the inner tube. Moreover, the term 'mounted' as used in the context of the medical device being mounted on the medical device receiving region is intended to include the case where the medical device is in contact with the medical device receiving region of the inner tube as well as the case where the medical device surrounds at least a portion of the medical device mounting region although it is not actually in contact with said region of the inner tube. An example of the former is as a stent crimped onto the inner tube while an example of the latter is a self expanding stent which is maintained in place about the inner tube by a sheath.

Further, although the rolling retractable sheath has been referred to as being disposed concentrically about the inner tube, the invention further contemplates the possibility of the rolling retractable sheath being disposed non-concentrically about the inner tube.

The present invention is also directed to methods of delivering a medical device, such as those described above, to a desired bodily location using any of the inventive devices described herein. One such method comprises the steps of providing one of the above-described medical device delivery systems and a medical device and mounting the medical device on the medical device mounting region of the system. The medical device delivery system is then percutaneously inserted in a bodily lumen containing a bodily fluid. Where the sheath is made of a porous material, bodily fluids may pass through the sheath so as to self-prime the medical device delivery system. The medical device is traversed through the bodily lumen until the desired bodily location is reached at which point the rolling retractable sheath is retracted proximally so as to expose the medical device. The medical device delivery system is then withdrawn from the bodily lumen.

In particular, this method may be used to deliver a self-expanding stent to a desired bodily location. Upon retraction of the sheath, the stent self-expands and the delivery system is then withdrawn. FIG. 6 shows one such suitable stent 458 for use with the present invention. Other medical devices such as balloon or mechanically expandable stents may similarly be delivered and deployed. In this case of the balloon expandable stent, the delivery system must be modified to include a balloon mounted over the inner tube and under at least a portion of the stent and to further include suitable tubes to allow for inflation of the balloon, as is well known in the art. Other medical devices that may be delivered by using the above method include grafts and vena cava filters.

Figure 11:
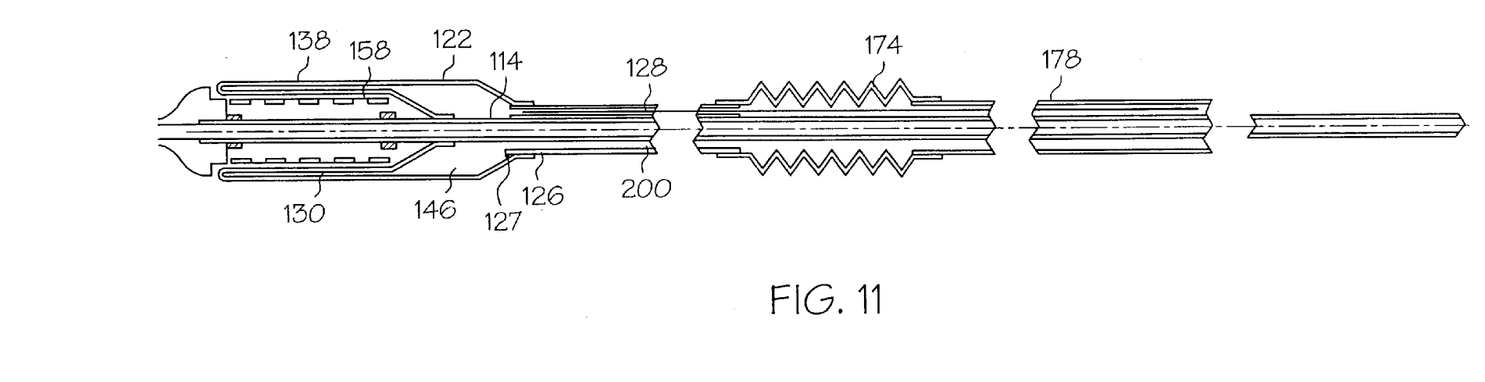
FIG. 11 shows a schematic longitudinal cross-section view of the distal end of another embodiment of the present inventive medical device delivery system.

The embodiment shown in FIG. 11 is substantially similar to the embodiment shown in FIG. 1a. As previously stated a retraction device 126 is attached to rolling retractable sheath 122. Retraction device 126 comprises a pull collar 127 operably attached to a pull-wire 128 which extends to the proximal end of the medical device delivery system. Pull collar 127 is affixed to distal outer tube 178. The distal outer tube is, in turn, connected to the rolling sheath. The pull wire may be made of suitable material including stainless steel.

In the embodiment shown in FIG. 11 however, chamber 146 is not sealed by the presence of pull collar 127 between the outer tube 128 and inner tube 114. In the present embodiment chamber 146 is in fluid communication with inflation lumen 200. By inflating chamber 146 with a fluid supplied through lumen 200, the sheath 122 may be utilized as a dilation balloon.

In order to effectively utilize the sheath 122 as a dilation balloon prior to stent delivery, the sheath must be prevented from retraction off of the stent 158 during inflation of chamber 146. During inflation of the sheath 122, retraction device 126 acts as a stiffening member to hold the sheath 122 in place thereby preventing any proximal movement or retraction of the sheath 122. The sheath 122 may be inflated prior to stent delivery in order to clear protrusions of plaque or other stenosis.

After the sheath has been inflated, the chamber 146 may be evacuated of fluid via the inflation lumen 200 and the retraction device 126 drawn proximally in order to pull back the sheath of the stent 158. Alternatively, the retraction device 126 may be relaxed to allow the presence of the fluid within chamber 146 to draw back the sheath in the manner previously described above.

To prevent distortion of the stent 158 which may potentially result from inflation of the sheath 122, the sheath is preferably constructed so that the outer wall 138 of the sheath is be composed of a higher compliance material than the inner wall 130. In addition, inner wall 130 may be positioned immediately adjacent to stent 158 with no space provided therebetween.

When the sheath 122 is used as a dilation balloon the sheath must be at least partially composed of a suitable balloon or expandable material. Preferably, sheath 122 is at least partially composed of polyethylene or polyolefin copolymers such as SURLYN™.

While several specific embodiments of the present invention have been described, the invention is directed more generally toward the use of rolling membranes in the manner described above in any other suitable catheter design not specifically described herein including over-the-wire, fixed-wire and rapid-exchange catheters.

In an over-the-wire embodiment, the inner tube extends proximally to a manifold and a guide wire may be inserted into the inner tube from the proximal end, the guide wire extending to the distal end of the system. The medical device delivery system may then ride on the guidewire.

In the case of the fixed-wire design, the guidewire is fixedly attached to the medical device delivery system. A fixed-wire delivery system is described in U.S. Pat. No. 5,702,364 to Euteneuer et al., incorporated herein in its entirety by reference, and may be suitably modified for use with the inventive medical device delivery system.

Similarly, a rapid exchange delivery system is described in U.S. Pat. No. 5,534,007 to St. Germain et al., incorporated herein in its entirety by reference, and may be suitably modified for use with the inventive medical device delivery system. Specifically, the rapid-exchange version may be realized by having the inner tube terminate in a guide wire port in a location along the system distal to the proximal end of the system to allow for insertion of a guide wire therein. In the rapid-exchange embodiment, only a portion of the medical device delivery system rides on a guidewire. Typically, the usable length of the medical device delivery system is approximately 135 cm. For a rapid-exchange medical device delivery system, the distance from where the guide wire accesses the inner tube to the distal tip will be approximately 5 cm to 45 cm.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A medical device delivery system comprising:
   an inner tube, having a distal region and a proximal region, the inner tube having a medical device mounting region at the distal region for mounting a medical device thereon;
   an outer tube, at least partially disposed about the inner tube;
   a rolling retractable sheath for retaining a medical device about the inner tube and for dilitation of a body vessel, the sheath having a proximal end and a distal end, the sheath disposed about the inner tube, the sheath having an inner wall attached to the inner tube proximal to the medical device mounting region and an outer wall, the inner wall extending distally and attached to the outer wall, the outer wall extending proximally and attached to the outer tube, the sheath defining a chamber, the chamber being in fluid communication with an inflation lumen, the sheath having an uninflated state and an inflated dilitation state.

2. The medical device delivery system of claim 1 wherein the outer tube further comprises a retraction device, the retraction device retaining the rolling retractable sheath in a delivery position when the rolling retractable sheath is in the inflated state, the retraction device moving the outer wall in a proximal direction relative to the inner wall to expose the medical device mounting region, the retraction device operably connected to the outer wall of the rolling retractable sheath.

3. The medical delivery device of claim 2 wherein the retraction device further comprises a catheter having proximal and distal ends and a lumen therein for receiving the inner tube therein, the distal end of the inner tube extending beyond the distal end of the catheter, the outer wall of the rolling retractable sheath attached to the distal end of the catheter.

4. The medical device delivery system of claim 1 wherein the inner and outer walls are adhesively bonded together at an end of the rolling double walled sheath.

5. The medical device delivery system of claim 1 wherein the inner and outer walls are mechanically joined together at an end of the rolling double walled sheath.

6. The medical device delivery system of claim 1 wherein the inner wall of the rolling retractable sheath is formed of at least a first material and the outer wall is formed of at least a second material different from the first material.

7. The medical device delivery system of claim 1 wherein the inner wall has a lower compliance than the outer wall.

8. The medical device delivery system of claim 1 wherein the outer wall of the sheath is thinner than the inner wall of the sheath.

9. The medical device delivery system of claim 1 wherein the inner and outer walls of the sheath are obliquely disposed relative to each other.

10. The medical device delivery system of claim 1 further comprising a lubricant applied to at least a portion of one or more of the inner and outer walls so as to reduce friction between the inner and outer walls.

11. The medical device delivery system of claim 1 further comprising a medical device selected from the group consisting of stents, grafts and vena cava filters, the medical device mounted on the medical device mounting region of the inner tube.

12. The medical device delivery system of claim 1 wherein the medical device is a stent and the stent is self-expandable.

13. The medical device delivery system of claim 1 configured for use in a mode selected from the group consisting of fixed-wire mode, over-the-wire mode and rapid-exchange mode.

14. A method of delivering a stent to a desired bodily location comprising the steps of:

providing a medical device delivery system as in claim 1;

providing a self-expanding stent;

mounting the stent on the medical device mounting region of the medical device delivery system;

percutaneously inserting the medical device delivery system in a bodily lumen containing a bodily fluid, traversing the bodily lumen until the desired bodily location is reached;

inflating the chamber of the rolling retractable sheath with a fluid;

removing the fluid from the chamber through the inflation lumen;

retracting the rolling retractable sheath proximally so as to expose the stent to self-expand; and withdrawing the medical device delivery system from the bodily lumen.

15. The medical device delivery system of claim 2, the retraction device further comprising a pull wire.

16. The medical device delivery system of claim 2, the retraction device further comprising an outer sheath.

17. The medical device delivery system of claim 1 wherein the inner wall and the outer wall are integrally formed.

* * * * *